United States Patent
Zilberman et al.

(10) Patent No.: US 7,091,270 B2
(45) Date of Patent: Aug. 15, 2006

(54) PENTABROMOBENZYL ALKYL ETHERS AND THEIR USE AS FIRE RETARDANTS

(75) Inventors: Joseph Zilberman, Haifa (IL); Alon Tavor, Omer (IL); Dorit Canfi, Haifa (IL); David Ioffe, Haifa (IL); Grigory Titelman, Haifa (IL); Samuel Bron, Yoqneam (IL); Olga Weinberg, Haifa (IL)

(73) Assignee: Bromine Compounds Ltd., Beer-sheva (IL)

( * ) Notice: Subject to any disclaimer, the term of this patent is extended or adjusted under 35 U.S.C. 154(b) by 0 days.

(21) Appl. No.: 10/502,267

(22) PCT Filed: Jan. 23, 2000

(86) PCT No.: PCT/IL03/00058

§ 371 (c)(1),
(2), (4) Date: Jan. 25, 2005

(87) PCT Pub. No.: WO03/064361

PCT Pub. Date: Aug. 7, 2003

(65) Prior Publication Data

US 2005/0124746 A1 Jun. 9, 2005

(30) Foreign Application Priority Data

Jan. 31, 2002 (IL) ..................... 147945

(51) Int. Cl.
*C08K 5/06* (2006.01)

(52) U.S. Cl. ............... 524/369; 524/464; 524/465; 524/466; 524/469; 568/588; 568/610; 568/656; 568/663

(58) Field of Classification Search ............... 524/369, 524/464–466, 469; 568/588, 610, 656, 663
See application file for complete search history.

(56) References Cited

U.S. PATENT DOCUMENTS

| 4,119,612 A | 10/1978 | Vollkommer et al. |
| 4,212,996 A * | 7/1980 | Petersen et al. ............ 568/639 |
| 5,078,918 A | 1/1992 | Fishler |

FOREIGN PATENT DOCUMENTS

EP 344700 12/1989

OTHER PUBLICATIONS

International Search Report for corresponding PCT application (3 pages).
International Preliminary Examination Report for corresponding PCT application (7 pages).
Chemical Abstracts XP002241771 & Shishkin, V.N.: Reactions with 2,3,4,5,6-Pentabromobenzyl Alkoxides Russian Journal of Organic Chemistry, vol. 38, No. 5, 2002, pp. 709-712.

* cited by examiner

*Primary Examiner*—Peter Szekely
(74) *Attorney, Agent, or Firm*—Roach Brown McCarthy & Gruber, P.C.; Kevin D. McCarthy

(57) ABSTRACT

The present invention provides novel pentabromobenzyl alkyl ethers serving as highly effective flame retardants in polymers. The invention further provides a fire retarded polymer composition comprising said pentabromobenzyl alkyl ethers.

20 Claims, No Drawings

PENTABROMOBENZYL ALKYL ETHERS AND THEIR USE AS FIRE RETARDANTS

FIELD OF THE INVENTION

The present invention provides novel pentabromobenzyl alkyl ethers serving as highly effective flame retardants in polymers. The invention further provides a fire retarded polymer composition comprising said pentabromobenzyl alkyl ethers. The terms fire retardants and flame retardants are used herein synonymously.

BACKGROUND OF THE INVENTION

Compounds containing a pentabromobenzyl moiety are known to be flame retardants. Pentabromobenzyl acrylate (EP 481126), pentabromobenzyl terephthalate (DE 33 20 333), and pentabromobenzyl tetrabromophthalate (EP 47866) are reported to be used in flame retardant polymer compositions. All the above mentioned compounds are esters of carboxylic acids. It is generally known that the ester group is rather unstable to hydrolysis, especially in the presence of acids and bases. This hydrolytic decomposition of esters precludes their use in a great number of applications.

While it is generally recognized that compositions containing bromine improve the flame retardancy of polymers, many bromine-containing compounds are unsatisfactory due to their instability. Such compounds are known to undergo dehydrobromination when incorporated in polymers.

Therefore there is a demand for fire retardants retaining their stability against hydrolysis, especially in the presence of acids and bases. In addition, there is a demand for bromine-containing fire retardants having stability against dehydrobromination when incorporated in polymers.

It is an object of present invention to provide a bromine-containing fire retardant, which has excellent fire-retardancy properties.

It is another object of present invention to provide such fire retardant retaining its stability against hydrolysis and/or decomposition in the presence of an acid or a base.

It is yet a further object of present invention to provide such fire retardant eliminating the undesired dehydrobromination process when incorporated in polymers.

It is yet a further object of present invention to provide fire retarded polymeric and polymer-containing compositions comprising such bromine-containing fire retardant.

The present invention provides novel pentabromobenzyl alkyl ethers possessing highly satisfactory flame retarding characteristics (properties) while retaining their stability against undesired processes, such as dehydrobromination and hydrolysis. The invention further provides polymeric and polymer-containing compositions containing the said novel pentabromobenzyl alkyl ethers that exhibit excellent fire retardancy.

Other objects and advantages of the invention will become apparent as the description proceeds.

SUMMARY OF THE INVENTION

The present invention provides a novel pentabromobenzyl alkyl ether of the formula:

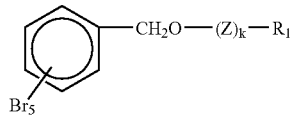

wherein:
Z represents the group $-(Y-O)_n-$, wherein Y is a linear or branched $-(C_2-C_8)$alkylene-, preferably $-CH_2CH_2-$ and $-CH_2CH(CH_3)-$;
n represents an integer from 2 to 4;
k may be 0 or 1;
$R_1$ represents hydrogen, a linear or branched $-(C_1-C_{10})$alkyl, a linear or branched $-(C_2-C_{10})$alkylene-OH, allyl, or 1,2-dibromopropyl; provided that when k is zero $R_1$ represents a linear or branched $-(C_4-C_{10})$alkyl or a linear or branched $-(C_2-C_{10})$alkylene-OH and when k is 1, $R_1$ represents hydrogen, a linear or branched $-(C_1-C_4)$alkyl, allyl or 1,2-dibromopropyl.

It further provides a process for the preparation of said novel compounds by the reaction of aliphatic mono-or di-alcohols or the corresponding metal alcoholates with pentabromobenzyl halide, preferably bromide. The pentabromobenzyl alkyl ethers of this invention possess good hydrolytic and thermal stability and are useful as flame retardants in thermoplastic and thermosetting resins. The present invention further provides a fire retarded polymeric and polymer-containing compositions comprising said novel pentabromobenzyl alkyl ethers.

All the above and other characteristics and advantages of the invention will be better understood through the following illustrative and non-limitative detailed description of the preferred embodiments thereof.

DETAILED DESCRIPTION OF PREFERRED EMBODIMENTS

The pentabromobenzyl alkyl ethers of the present invention are prepared by the reaction of pentabromobenzyl halide, preferably bromide (PBBBr) with an aliphatic mono- or di-alcohol (or the corresponding metal alcoholate), in the presence or absence of a base. Aliphatic alcohols (or the corresponding metal alcoholates) which are reacted with pentabromobenzyl halide, preferably PBBBr, to obtain the pentabromobenzyl alkyl ethers of present invention may be represented by the formula:

wherein Z, $R_1$ and k are as defined above.

Aliphatic alcohols of the above formula used in the process for preparing the compounds of present invention include, inter alia, glycols such as ethylene glycol, diethylene glycol, triethylene glycol, tetraethylene glycol, propylene glycol, dipropylene glycol, tripropylene glycol, tetrapropylene glycol, and monoethers of these glycols such as methyl, ethyl, propyl, isopropyl, butyl, isobutyl and allyl ether. Other aliphatic alcohols used in said process may be straight chained and branched alcohols such as butanols, pentanols, hexanols, octanols, nonanols, decanols.

Aliphatic di-alcohols also applicable, for example 1,3-propane diol, 1,4-butane diol, 1,5-pentane diol, 1,6-hexane diol, 1,7-heptane diol, 1,8-octane diol, 1,9-nonane diol, 1,10-decane diol.

In a preferred embodiment the reaction of PBBBr and the aliphatic alcohol is carried out in the presence of a strong base such as sodium hydroxide or potassium hydroxide, in a medium of either an organic solvent or an excess aliphatic alcohol. The organic solvent is selected from aromatic compounds. Especially suitable aromatic solvents are chlorobenzene, ortho-dichlorobenzene, bromobenzene, mesitylene, and in particular, toluene and xylene.

An effective amount of the base employed in the process is in a range of 1–1.5 mol per 1 mol PBBBr, and preferably 1–1.2 mol.

When an aromatic solvent is used, the amount of a glycol monoether of the formula HO-$(Z)_k$-$R_1$, wherein Z represents —(Y—O)—, or of an alcohol in which k is zero, may be in the range of 1–4 mol alcohol, and preferably between 1.5–3 mol, per 1 mol PBBBr. When the reaction is carried out in an excess of reacting alcohol of the formula HO-$(Z)_k$-$R_1$ also used as a solvent, the amount of alcohol is preferably expressed in weight percent in relation to the amount of PBBBr. Thus, the excess of alcohol in such cases is from 200 up to 1000% by weight, and preferably 400–700% by weight, over the amount of PBBBr used. An excess of alcohol below 200% by weight makes carrying out the reaction rather cumbersome and problematic due to the difficulty of stirring the highly concentrated suspension of PBBBr in the alcohol. Using an excess of alcohol greater than 1000% by weight over the amount of PBBBr is inexpedient due to the need of recycling a large quantity of alcohol.

Regardless of the presence or absence of the aromatic organic solvent the amount of glycol of the formula HO-$(Z)_k$-$R_1$, wherein Z represents —(Y—O)$_n$—, ($R_1$ is H and Y and n are as defined above) or dialcohols of the formula HO-$(Z)_k$-$R_1$, wherein k is zero and $R_1$ represents a linear or branched —$(C_2$–$C_{10})$alkylene-OH, comprises between 5–18 mol, and preferably between 10–15 mol per 1 mol PBBBr. The relatively large excessive amounts of these alcohols are required for minimizing the formation of undesirable diethers, namely di-pentabromobenzyl ethers of glycols and diols. Using a molar ratio greater than 18 mol alcohol per 1 mol PBBBr is inexpedient due to the need to recycle a larger quantity of alcohol.

Said reactions are carried out at a temperature of between 40 and 150° C., and preferably between 50 and 110° C. Applying a temperature lower than 40° C. resulted in a low yield. On the other hand, applying a temperature higher than 150° C. is not advisable since at such temperatures undesirable decomposition products are formed in the presence of a strong base.

Sodium or potassium hydroxide is employed in a solid form. Water should be eliminated from the reaction mixture as much as possible. When aqueous solutions of hydroxides are used the main reaction products are pentabromobenzyl alcohol and di-pentabromobenzyl ether.

The reaction may also be conducted without a base. However, due to the fact that PBBBr is considerably less reactive towards alcohols in the absence of a strong base, the reaction must be carried out at a temperature of between 170 and 220° C. Applying such high temperatures favors the formation of undesired decomposition products.

The following examples illustrate specific embodiments of both the preparation of certain compounds of the invention and the utility of these compounds as flame retardants in various polymer resins. The following examples should not be construed as limiting the scope thereof.

EXAMPLE 1

A 2 liter reactor, equipped with a mechanical stirrer, a thermometer and a reflux condenser, is charged with PBBBr (212 g, 0.37 mol) and 2-methoxyethanol (700 g, 10 mol). The slurry formed is heated to 105° C., followed by addition of potassium hydroxide powder (25.7 g, 0.39 mol). The resulting mixture is heated for 3 hours at 105° C., with vigorous stirring until the PBBBr conversion is complete (confirmed by HPLC analysis). The solids are filtered at room temperature and washed with water (300 g) to remove potassium bromide. After vacuum drying of the remaining solid, there are obtained 182 g (83% of theoretical) of 1-methoxy-2-pentabromobenzyloxyethane [pentabromobenzyl-O—$CH_2$–$CH_2OCH_3$] in the form of a white solid powder, melting point 145–146° C. HPLC analysis shows the purity to be 100% (area %). The unreacted 2-methoxyethanol is recovered by stripping off the ethanol and can be used repeatedly.

EXAMPLE 2

A 2 liter reactor, equipped with a mechanical stirrer, a thermometer and a reflux condenser, is charged with PBBBr (500 g, 0.88 mol), 2-butoxyethanol (212 g, 1.8 mol) and toluene (800 ml). The slurry formed is heated to 55° C., followed by addition of sodium hydroxide powder (38 g, 0.9 mol). The resulting mixture is heated for 3 hours at 55° C., with vigorous stirring until the PBBBr conversion is complete (confirmed by HPLC analysis). The final reaction mixture is cooled to room temperature, sodium bromide formed is filtered off and the toluene is fully stripped off. The remaining viscous liquid is mixed with ethanol (1 l) at 75° C. and a by-product constitutes bis-(pentabromobenzyl) ether which does not dissolve in ethanol, is removed by hot filtration. After crystallization, filtration and vacuum drying, there is obtained 426 g (80% of theoretical) of 1-butoxy-2-pentabromobenzyloxyethane [pentabromobenzyl-O—$CH_2CH_2O(CH_2)_3CH_3$] in the form of a white solid powder, melting point 67° C. The HPLC analysis shows the purity to be 100% (area %). The unreacted 2-butoxyethanol is recovered by stripping off the ethanol and can be used repeatedly.

EXAMPLE 3

A 0.25 liter reactor, equipped with a mechanical stirrer, a thermometer, and a reflux condenser, is charged with the monomethyl ether of diethylene glycol (12 g, 0.1 mol), NaOH (1.6 g, 0.038 mol) and ortho-xylene (80 ml). The reactor contents are heated to 70° C., followed by addition of PBBBr (20 g, 0.035 mol). The resulting mixture is heated for 2 hours at 70° C. with vigorous stirring until the PBBBr conversion is complete (HPLC analysis). The treatment of the final reaction mixture is carried out as described in Example 1. There is obtained 15.9 g (75% of theoretical) of 1-(penta-bromophenyl)-2,5,8-trioxanonane [pentabromobenzyl-O—$(CH_2CH_2O)_2CH_3$] in the form of a white solid powder, melting point 83° C. HPLC analysis shows the purity to be 99.5% (area %).

EXAMPLE 4

A 2 liter reactor, equipped with a mechanical stirrer, a thermometer, and a reflux condenser, is charged with diethylene glycol (637 g, 6 mol) and solid sodium hydroxide (16.8 g, 0.42 mol). The mixture is heated to 80° C., followed by portion-wise addition of PBBBr (226.2 g, 0.4 mol) over a period of 1.5 h. The reaction slurry is heated for one more hour with vigorous stirring until the PBBBr conversion is complete (confirmed by HPLC analysis). Ethanol (0.75 l) is added and the precipitated solid is washed thoroughly with 1 l of 50% aq. ethanol. After vacuum drying there is obtained 217 g (92% of theoretical) of 3,6-dioxa-7-(pentabromophenyl)-heptanol-1[pentabromobenz yl-O—$(CH_2CH_2O)_2H$] in the form of a white solid, melting point 117–120° C. HPLC analysis shows the purity to be 98% (area %). The product contains 2% diethylene glycol dipentabromobenzyl ether.

EXAMPLE 5

A 2 liter reactor, equipped with a mechanical stirrer, a thermometer and a reflux condenser, is charged with PBBBr (453 g, 0.8 mol) and 1,6-hexane diol (1134 g, 9.6 mol). The slurry formed is heated to 85° C., followed by addition of sodium hydroxide powder (36 g, 0.88 mol). The resulting mixture is heated at 85° C. for 4 hours with vigorous stirring until the PBBBr conversion is complete (confirmed by HPLC analysis). The excess diol is distilled off under vacuum (1 mm Hg, 100–105° C.) and can be used repeatedly. The residue is treated with refluxing acetonitrile (1 l) followed by hot filtration to remove sodium bromide and bis(pentabromobenzyl) ether. After crystallization, filtration and vacuum drying there is obtained 337 g (70% of theoretical) of 6-(pentabromobenzyloxy)-hexanol-1 [pentabromobenzyl-O—$(CH_2)_6OH$] in the form of a white solid powder, melting point 81–83° C. HPLC analysis shows the purity to be 98% (area %).

EXAMPLE 6

A 1 liter reactor, equipped with a mechanical stirrer, a thermometer and a reflux condenser, is charged with 2-ethylhexanol-1 (68.3 g, 0.525 mol), toluene (400 ml) and potassium hydroxide (17.3 g, 0.26 mol). The reactor contents are heated to 90° C., followed by addition of PBBBr (102 g, 0.18 mol). The reaction mixture is heated for 5 hours at 90° C. with vigorous stirring until the PBBBr conversion is complete (confirmed by HPLC analysis). The final reaction mixture is cooled to room temperature, sodium bromide is filtered off and the toluene is fully stripped. The remaining viscous liquid is mixed with 0.15 l ethanol-water (80:20) at 75° C. and bis(pentabromobenzyl) ether is removed by hot filtration. After crystallization in an ice bath, filtration and vacuum drying there is obtained 88.7 g (80% of theoretical) of pentabromobenzyl 2-ethylhexyl ether [pentabromobenzyl-O—$CH_2CH(C_2H_5)$—$(CH_2)_3CH_3$]. The final product is in the form of a white wax at room temperature. HPLC analysis shows the purity to be 99% (area %).

EXAMPLE 7

A 0.25 liter reactor, equipped with a mechanical stirrer, a thermometer, a reflux condenser and a Dean-Stark trap, is charged with 2-allyloxyethanol (7.2 g, 0.07 mol), toluene (100 ml) and sodium hydroxide (1.5 g, 0.037 mol). The reactor contents are heated to reflux and the water formed is removed as an azeotrop with toluene. After cooling down of the reactor contents to 90° C. PBBBr (20 g, 0.035 mol) is added and after heating at 90° C. for 1 hour the PBBBr conversion is complete (confirmed by HPLC analysis). The final reaction mixture is cooled to room temperature, sodium bromide is filtered off and the toluene is fully stripped. The crystallization of the residue from ethanol-dichloroethane (3:1) affords 16.8 g (81% of theoretical) of 1-allyloxy-2-pentabromobenzyloxyethane[pentabromobenzyl-O—$CH_2CH_2OCH_2CH$=$CH_2$] in the form of a beige solid powder, melting point 87–88° C. HPLC analysis shows the purity to be 99.6% (area %).

EXAMPLE 8

A 0.25 liter reactor, equipped with a mechanical stirrer, a thermometer, a reflux condenser and a Dean-Stark trap connected to a vacuum pump, is charged with monomethyl ether of dipropylene glycol (26.6 g, 0.18 mol), toluene (100 ml) and sodium hydroxide (4 g, 0.1 mol). The reactor contents are heated to reflux (105° C.) under a reduced pressure of 810 mbar and the water formed is removed as an azeotrope with toluene. The reactor contents are cooled down while refluxing by gradually reducing the pressure to 65 mbar. When the temperature is 35° C. the pressure in the reactor is allowed to equalize to atmospheric pressure, and PBBBr (50 g, 0.088 mol) is added. The reaction mixture is heated at 70° C. for 2 hours, with vigorous stirring, until no PBBBr is detected (HPLC analysis). The reaction mixture is cooled to room temperature and neutralized to pH 7 with concentrated hydrochloric acid. The sodium bromide formed is filtered off and the toluene is fully stripped. The excess monomethyl ether of dipropylene glycol is distilled off at 80–120° C. (15 mbar). The hot mixture is filtered to remove traces of the by-product bis(pentabromobenzyl) ether. The residue is washed twice with 50 ml water at 70° C. After vacuum drying 51.5 g (92% yield) of dipropylene glycol methyl pentabromobenzyl ether [pentabromobenzyl-O—$(C_3H_6O)_2CH_3$] is obtained in the form of a clear amber liquid. HPLC analysis shows the purity to be above 99% (area %). The product is a mixture of isomers.

EXAMPLE 9

A 2 liter reactor, equipped with a mechanical stirrer, a thermometer, and a reflux condenser attached to a Dean-Stark trap, is charged with dipropylene glycol (322 g, 2.4 mol), toluene (600 ml) and sodium hydroxide (18 g, 0.44 mol). The reactor contents are heated to reflux and the water formed is removed as an azeotrope with toluene. After cooling the reactor contents to 50° C., PBBBr (226 g, 0.4 mol) is added. The reaction mixture is heated at 70° C. for 2 hours, with vigorous stirring, until no PBBBr is detected (HPLC analysis). The final reaction mixture is cooled to room temperature and neutralized to pH 7 with concentrated hydrochloric acid. The toluene is fully stripped and the excess dipropylene glycol is then distilled off at 105–108° C. (1–2 mbar). The hot liquid residue is washed with 400 ml water four times at 80° C., and then filtered to remove traces of bis(pentabromobenzyl)ether. After vacuum drying 220 g (90% yield) of dipropylene glycol pentabromobenzyl ether [pentabromobenzyl-O—$(C_3H_6O)_2H$] is obtained in the form of a beige wax. HPLC analysis shows the purity to be above 99% (area %). The product is a mixture of isomers.

The novel compounds of the present invention are highly efficient flame retardants when incorporated into various polymers or polymer-containing compositions. In general, the novel compounds of present invention are useful as flame retardants in a wide variety of polymeric compositions such as, for example, chlorinated polyethylene, polyethylene, polypropylene, styrene resins, high-impact polystyrene, polyvinyl chloride, acrylonitrile-butadiene-styrene copolymer, flexible and rigid polyurethanes, epoxy resins, unsaturated polyester resins and the like. In particular, the compounds of present invention are highly effective flame retardants in polyurethanes. The novel compounds of the invention are also useful as fire retardants when incorporated into polymer-containing compositions. Such compositions as used herein are polymeric compositions that also comprise other constituents (other than the fire retardants of the invention). Such constituents may be, but are not limited to, catalysts, antioxidants, anti-dripping agents and the like. In the polymer-containing compositions the polymeric constituent may be any one of the above-mentioned polymers.

The amount of novel compound of present invention which is necessary for conferring commercially satisfactory flame retardancy to a particular polymer or polymer-containing composition may vary over a wide range. Usually, the flame retardant material of present invention is employed in an amount of between about 1 to 50% by weight of the polymer. Preferably, between about 3 to about 30% is used. In general, any suitable known method of incorporating flame retardants to polymer materials may be employed.

The following examples demonstrate the utility of the pentabromobenzyl alkyl ether of the present invention as a flame retardant in various polymers.

EXAMPLE 10

In this example polypropylene (block copolymer of polypropylene with propylene-ethylene rubber, Capilene SG-50, a trade mark of Carmel Olefins) in a granulated form was used as the polymer resin. Different pentabromobenzyl alkyl ethers, each in amount corresponding to 22 wt % of bromine and 11 wt % of antimony oxide as a synergist, were admixed with the polypropylene. Regular amounts of antioxidants and anti-dripping agents, when applied, were added to the mixture at the expense of the polymer. Mixing was done in a Brabender internal mixer of 55 cm$^3$ volume capacity at 50 rotations per minute and 190° C. for various periods. Specimens of 3.2 mm thickness were prepared by compression molding in a hot press at 200° C., cooling to room temperature and cutting into standard test pieces.

The flammability was tested by the limiting oxygen index method (hereinafter referred to as "LOI") in accordance with ASTM D-2863-99. LOI is defined as the minimum concentration of oxygen (% vol) in a mixture of oxygen and nitrogen that will just support combustion of the fire retarded polymer under the conditions of the test procedure. The utility of pentabromobenzyl alkyl ethers as flame retardants is shown in Table 1: all formulations containing pentabromobenzyl alkyl ethers have a significantly larger LOI than the neat polymer.

TABLE 1

| Flame retardant* | Wt. % | LOI, O$_2$ % |
|---|---|---|
| None | 0.0 | 16.7 |
| Ether of Example 1 | 30.8 | 23.5 |
| Ether of Example 2 | 33.7 | 23.0 |
| Ether of Example 5 | 34.4 | 22.8 |
| Ether of example 6 | 33.7 | 22.0 |

*Each formulation contains 22 wt % bromine

EXAMPLE 11

In this example, polystyrene (either a High Impact Polystyrene (HIPS)—Styron 472, a trade mark of Dow, or a Acryl-Butadiene-Styrene terpolymer (ABS)— Magnum 3404, a trade mark of General Electric) was used as the polymer resin. Different pentabromobenzyl alkyl ethers in various amounts corresponding to a bromine content of 6%, 11% or 12%, and antimony oxide as a synergist, as shown in Table 2, were admixed with the polymer in a granulated form. Regular amounts of antioxidants and anti-dripping agents, when applied, were added to the mixture at the expense of the polymer. Mixing was done in a Brabender internal mixer of 55 cm$^3$ volume capacity at 50 rotations per minute and 200° C. for the desired time. Specimens of 3.2 mm or 1.6 mm thickness were prepared by compression molding in a hot press at 200° C., cooling to room temperature and cutting into standard test pieces. The flammability was tested by the limiting oxygen index method (as described above) in accordance with ASTM D-2863, and by the UL-94 test (Underwriters Laboratories) with bottom ignition for two successive 10-second intervals by a standard burner flame. Five test-pieces of each composition were tested under the conditions of the UL-94 procedure. A wide range of flame retardancy of styrene polymers can be achieved (UL-94 rating V-2 or V-0) at 1.6 and 3.2 mm thickness, indicating that the novel pentabromobenzyl alkyl ethers of present invention provides a high level of fire retardancy efficiency.

TABLE 2

| Flame retardant | Polymer type | Ether Wt % | Bromine Wt % | Sb$_2$O$_3$ Wt % | LOI O$_2$ % | UL-94 3.2 mm | UL-94 1.6 mm |
|---|---|---|---|---|---|---|---|
| None | ABS | 0 | 0 | 0 | 18.0 | NR | NR |
| None | HIPS | 0 | 0 | 0 | 17.8 | NR | NR |
| Ether of Example 1 | HIPS | 15.4 | 11.0 | 6.0 | 24.4 | V-0 | |
| Ether of Example 1 | ABS | 15.4 | 11.0 | 6.0 | 24.8 | V-0 | |
| | HIPS | 16.8 | 12.0 | 6.0 | 25.1 | | V-0 |
| Ether of Example 2 | HIPS | 16.9 | 11.0 | 6.0 | 23.8 | V-0 | |
| | HIPS | 9.2 | 6.0 | 3.0 | 21.8 | | V-2 |
| Ether of Example 6 | HIPS | 16.9 | 11.0 | 6.0 | 23.2 | V-0 | |
| | HIPS | 9.2 | 6.0 | 3.0 | 21.4 | | V-2 |
| Ether of Example 5 | HIPS | 17.2 | 11.0 | 6.0 | 24.0 | V-0 | |
| Ether of Example 5 | ABS | 17.2 | 11.0 | 6.0 | 24.8 | V-0 | |
| | HIPS | 18.2 | 12.0 | 6.0 | 24.7 | | V-0 |
| Ether of Example 4 | ABS | 17.9 | 12.0 | 6.0 | — | | V-0 |
| Ether of Example 4 | HIPS | 17.9 | 12.0 | 6.0 | — | | V-0 |

EXAMPLE 12

In this example, standard flexible polyurethane foam was used as polymeric matrix. Different pentabromobenzyl alkyl ethers were added in various amounts as shown in Table 3. The ethers were added as a 75:25 mixture with an isopropylated triphenyl phosphate ester (Phosflex 31 L ex Akzo Nobel). The polyol (100 parts polyol per one hundred parts resin (phr)), water (4.2 phr), surfactant (1.1 phr), flame retardant and catalysts were weighed and mixed using a high speed mixer at about 3000 rpm. The polyol used in this example was a polyether with terminal hydroxyl groups. The molecular weight was about 4800 and the hydroxyl number was 46 mg KOH/g. TDI (54.8 phr) was added under the hood, mixed for 10 sec including the pouring time (the timer was started when TDI was added). The TDI is a 80:20 mixture of 2,4- and 2,6-toluene-diisocyanate. The mixture was then quickly poured into a shoebox with dimensions 33×20×20 cm$^3$. The usual cream time (from the moment TDI was added till the foam started to rise) was about 15 sec for all formulations. The usual blow off time (measured from the moment TDI was added till the foam stopped rising and CO$_2$ was suddenly released through the upper surface) was about 130–140 sec. The resulting bun was let to cool under the hood for 24 hours, dismantled from the shoebox and cut into 30×7.5×1.27 cm³ specimens. At least 10 specimens were tested, 5 specimens from each formulations after conditioning at room temperature and 50±5% relative humidity for 24 hours, and another set of 5 specimens from each formulation after aging for 24 hours at 104° C. The specimens were subjected to the vertical burning test in a special cabinet as required by the California TB 117, Section A, Part I. The flammability was tested by bottom ignition for a 12-second interval using a vertical burner butane flame with a length of 40 mm. For a formulation to pass the test, it is required that the maximum char length would be below 20 cm, the average char length below 15 cm, the average after-flame time below 5 sec, the maximum after-flame time below 10 sec, and the maximum after-glow time below 15 sec. These requirements should be met for both sets of specimens. All the formulations containing the novel pentabromobenzyl alkyl ethers of present invention passed the California TB 117, Section A, Part I test, indicating that they are able to provide a high level of fire retardancy efficiency to flexible polyurethane foams.

TABLE 3

| Flame retardant | Ether phr | Phosflex 31L phr | Bromine Wt % | Cal 117 RT conditioning | Cal 11 104° C. aging |
|---|---|---|---|---|---|
| None | 0 | | 0 | fail | fail |
| Ether of Example 2 | 8.19 | 2.73 | 3.1 | pass | pass |
| Ether of Example 6 | 8.19 | 2.73 | 3.1 | pass | pass |
| Ether of Example 8 | 8.45 | 2.82 | 3.1 | pass | pass |
| Ether of Example 9 | 8.19 | 2.73 | 3.1 | pass | pass |

While the invention has been described herein above with regard to certain illustrative, specific embodiments, it should be pointed out that many modifications and variations are possible in the light of the above teaching. It is understood therefore, that the invention may be practiced otherwise than as specifically described in the above examples without departing from the spirit and scope of the invention.

We claim:

1. A pentabromobenzyl alkyl ether of the formula:

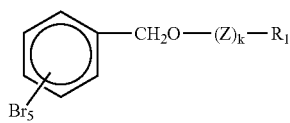

wherein:
Z represents the group $-(Y-O)_n-$, wherein Y is a linear or branched $-(C_2-C_8)$alkylene-;
n represents an integer from 2 to 4;
k may be 0 or 1;
$R_1$ represents hydrogen, a linear or branched $-(C_1-C_{10})$ alkyl, allyl, or 1,2-dibromopropyl; provided that when k is zero $R_1$ represents a linear or branched $-(C_4-C_{10})$ alkyl, and when k is 1 $R_1$ represents hydrogen, a linear or branched $-(C_1-C_4)$alkyl, allyl or 1,2-dibromopropyl.

2. A pentabromobenzyl alkyl ether according to claim 1, wherein Z represents a group selected from $-(C_2H_4O)n$ and $-(C_3H_6O)n$, wherein n represents 2.

3. A pentabromobenzyl alkyl ether according to claim 1, wherein k=1 and $R_1$ represents H, methyl or butyl.

4. A pentabromobenzyl alkyl ether according to claim 1, wherein k=0 and $R_1$ represents branched $(C_8)$alkyl.

5. A pentabromobenzyl alkyl ether according to claim 1, selected the group consisting of:
pentabromobenzyl-O—$(CH_2CH_2O)_2CH_3$;
pentabromobenzyl-O—$(CH_2CH_2O)_2H$;
pentabromobenzyl-O—$(CH_2)_6OH$;
pentabromobenzyl-O—$CH_2CH(C_2H_5)(CH_2)_3CH_3$;
pentabromobenzyl-O—$(C_3H_6O)_2$—$CH_3$, and
pentabromobenzyl-O—$(C_3H_6O)_2$—H.

6. A fire retarded polymeric or polymer-containing composition comprising a pentabromobenzyl alkyl ether of the formula:

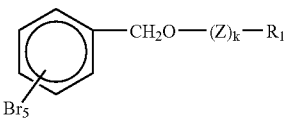

wherein:
Z represents the group $-(Y-O)_n-$, wherein Y is a linear or branched $-(C_2-C_8)$alkylene-;
n represents an integer from 2 to 4;
k may be 0 or 1;
$R_1$ represents hydrogen, a linear or branched $-(C_1-C_{10})$ alkyl, a linear or branched $-(C_2-C_{10})$alkylene-OH, allyl, or 1,2-dibromopropyl; provided that when k is zero $R_1$ represents a linear or branched $-(C_4-C_{10})$ alkyl or a linear or branched $-(C_2-C_{10})$alkylene-OH and when k is 1, $R_1$ represents hydrogen, a linear or branched $-(C_1-C_4)$alkyl, allyl or 1,2-dibromopropyl.

7. A fire retarded composition according to claim 6, wherein said polymer is selected from the group consisting of chlorinated polyethylene, polyethylene, polypropylene, styrene resins, high-impact polystyrene, polyvinyl chloride acrylonitrile-butadiene-styrene copolymer, flexible and rigid polyurethane, epoxy resins and unsaturated polyester resins.

8. A fire retarded composition according to claim 7, wherein said polymer is polypropylene.

9. A fire retarded composition according to claim 7, wherein said polymer is high impact polystyrene (HIPS).

10. A fire retarded composition according to claim 7, wherein said polymer is acryl-butadiene-styrene terpolymer (ABS).

11. A fire retarded composition according to claim 7, wherein said polymer is polyurethane.

12. A fire retarded composition according to claim 6, wherein said polymer is selected from the group consisting of polyurethane, polypropylene copolymer, high impact polystyrene (HIPS) and acryl-butadiene-styrene terpolymer (ABS), and said pentabromobenzyl alkyl ether is selected from the group consisting of:
pentabromobenzyl-O—$(CH_2CH_2O)_2CH_3$;
pentabromobenzyl-O—$(CH_2CH_2O)_2H$;
pentabromobenzyl-O—$(CH_2)_6OH$;
pentabromobenzyl-O—$CH_2CH(C_2H_5)(CH_2)_3CH_3$;
pentabromobenzyl-O—$(C_3H_6O)_2$—$CH_3$, and
pentabromobenzyl-O—$(C_3H_6O)_2$—H.

13. A fire retarded composition according claim 6, further comprising a metal oxide, preferably $Sb_2O_3$.

14. A process for the preparation of a pentabromobenzyl alkyl ether of the formula:

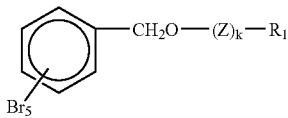

wherein:

Z represents the group $—(Y—O)_n—$, wherein Y is a linear or branched $—(C_2–C_8)$alkylene-;

n represents an integer from 2 to 4;

k may be 0 or 1;

$R_1$ represents hydrogen, a linear or branched $—(C_1–C_{10})$ alkyl, allyl, or 1,2-dibromopropyl; provided that when k is zero $R_1$ represents a linear or branched $—(C_4–C_{10})$ alkyl, and when k is 1 $R_1$ represents hydrogen, a linear or branched $—(C_1–C_4)$alkyl, allyl or 1,2-dibromopropyl, comprising reacting a glycol, a mono-, or di-alcohol of the formula $HO—(Z)_k—R_1$, or the corresponding metal alcoholate thereof, with a pentabromobenzyl halide.

15. The process of claim 14, wherein the pentabromobenzyl halide is pentabromobenzyl bromide.

16. The process of claim 14, wherein the reaction occurs in the presence of a base.

17. The process of claim 14, wherein the linear or branched $—(C_2–C_8)$alkylene— is selected from the group consisting of $—CH_2CH_2—$ and $—CH_2CH(CH_3)—$.

18. A fire retarded polymeric or polymer-containing composition of claim 6, wherein the linear or branched $—(C_2–C_8)$alkylene— is selected from the group consisting of $—CH_2CH_2—$ and $—CH_2CH(CH_3)—$.

19. A pentabromobenzyl alkyl ether according to claim 1, wherein the linear or branched $—(C_2–C_8)$alkylene— is selected from the group consisting of $—CH_2CH_2—$ and $—CH_2CH(CH_3)—$.

20. The method of using the compound of claim 1 as a fire-retardant.

* * * * *